United States Patent [19]
Sanghvi et al.

[11] Patent Number: 6,124,484
[45] Date of Patent: *Sep. 26, 2000

[54] RECOVERY OF TRIARYLMETHYL HALIDE PROTECTING GROUPS CLEAVED DURING OLIGONUCLEOTIDE SYNTHESIS

[75] Inventors: Yogesh S. Sanghvi, Encinitas; Zhiqiang Guo, San Marcos, both of Calif.

[73] Assignee: Isis Pharmaceuticals, Inc., Carlsbad, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/118,614

[22] Filed: Jul. 17, 1998

[51] Int. Cl.$^7$ ..................................................... C09B 11/04
[52] U.S. Cl. ........................ 552/115; 548/346.1; 548/476; 549/26; 549/388; 549/434; 549/435; 549/504; 552/101; 552/108
[58] Field of Search .................................. 552/101, 108, 552/115

[56] References Cited

U.S. PATENT DOCUMENTS

| 3,687,808 | 8/1972 | Merigan et al. | 195/28 |
| 5,563,220 | 10/1996 | Webber et al. | 525/333 |

FOREIGN PATENT DOCUMENTS

| 4306839 | 9/1994 | Germany . | |

OTHER PUBLICATIONS

Guo, Z., H.M. Pfundheller, and Y.S. Sanghvi. *Organic Process Research & Development*. 2, 415–417 (1998).

Bleasdale, C. et al., "4,4'–Dimethoxytrityl and 4–Monomethoxytrityl Tetrafluoroborate: Convenient Reagents for the Protection of Primary Alcohols Including Sugars", *J. Chem. Soc. Perkin Trans.*, 1990, 1, 803–805.

Brill, W., "Facile Methods to Recycle Nucleosides during Solid Phase Synthesis of Oligonucleotides", *Tetrahedron Letts.*, 1994, 35(19), 3041–3044.

Ciba Foundation Symposium 209, *Oligonucleotides as Therapeutic Agents*, John Wiley & Sons, 1997, 1–250.

Cook, P.D., "Medicinal chemistry of antisense oligonucleotides—future opportunities", *Anti–Cancer Drug Design*, 1991, 6, 585–607.

Delgado, C. et al., "The Uses and Properties of PEG–Linked Proteins", *Crit. Rev. in Therapeutic Drug Carrier Sys.*, 1992, 9, 249–304.

Ding et al., "Detritylation of mono– and di–saccharide derivatives using ferric chloride hydrate", *Carbohydrate Res.*, 1997, 303, 445–448.

Engels, "Selective Electrochemical Removal of Protecting Groups in Nucleotide Synthesis", *Angew. Chem. Int. Ed. Engl.*, 1979, 18(2), 148–149.

Englisch, U. et al., "Chemically Modified Oligonucleotides as Probes and Inhibitors", *Angew. Chem. Int. Ed. Eng.*, 1991, 30, 613–629.

Greene et al., "Use of the Naphthalene Radical Ion in Deblocking O–Methoxytrityl Nucleotide Derivatives", *Tetrahedron Lett.*, 1975, 25, 2081–2084.

Kohli et al., "The Triphenylmethyl (Trityl) Group and its Uses in Nucleotide Chemistry", *Tetrahedron Lett.*, 1980, 21, 2683–2686.

Kroschwitz, J.I., "Polynucleotides", *Concise Encyclopedia of Polymer Science and Engineering*, 1990, John Wiley & Sons, New York, 858–859.

Letsinger et al., "Selective Deprotection by Reductive Cleavage with Radical Anions", *J. Am. Chem. Soc.*, 1975, 97(24), 7197–7198.

Matteucci et al., "The Use of Zinc Bromide for Removal of Dimethoxytrityl Ethers from Deoxynucleosides", *Tetrahedron Lett.*, 1980, 21, 3243–3246.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Sanghvi et al., "Carbohydrates: Synthetic Methods and Applications in Antisense Therapeutics", in Carbohydrate Modifications in Antisense Research, ACS Symposium Series 580, ACS Publications, Washington, DC, 1994, Ch. 1, 1–22.

Scremin et al., "Stepwise Regeneration and Recovery of Deoxyribonucleoside Phosphoramidite Monomers during Solid–Phase Oligonucleotide Synthesis", *J. Org. Chem.*, 1994, 59, 1963–1966.

Yang et al., "Facile Selective Detritylation of 5'–Primary Alcohols of Pyrimidine Nucleosides Using Tetra–n–butylammonium Peroxydisulfate", *Heteroatom Chem.*, 1997, 8(5), 435–438.

Hayatsu, H et al., "Studies on Polynucleotides. LXXII. Deoxyribooligonuycleotide Synthesis on a Polymer Support", *Journal of the American Chemical Society*, 1967, 89, pp. 3880–3887.

Rathore, M et al., "A New Method for Synthesis of 4,4'–dimethoxytrityl Chloride", *Indian Journal of Chemistry*, 1995, 34B, pp. 634–635.

*Primary Examiner*—Michael G Ambrose
*Attorney, Agent, or Firm*—Woodcock Washburn Kurtz Mackiewicz & Norris LLP

[57] ABSTRACT

The present invention provides a method for the preparation of triarylmethyl protecting group reagents. The reagents are prepared from reaction effluent from the cleavage step of oligonucleotide synthetic regimes.

39 Claims, 2 Drawing Sheets

Figure 1

Solid Phase Oligonucleotide Synthesis

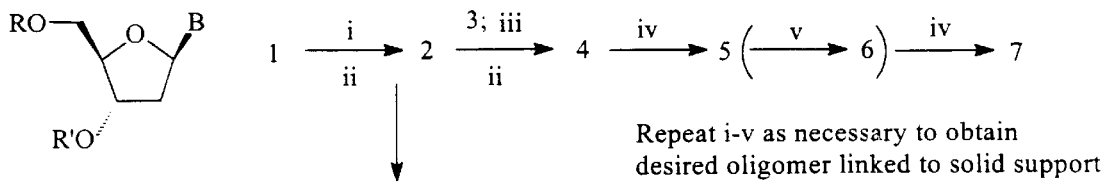

Repeat i-v as necessary to obtain desired oligomer linked to solid support effluent containing orange-red DMT cation:

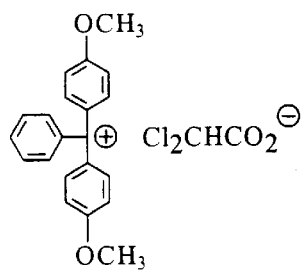

in $CH_2Cl_2$
and excess $Cl_2CHCO_2H$

|   | R | R' |
|---|---|---|
| 1 | DMT | L/SS |
| 2 | H | L/SS |
| 3 | DMT | 5'-Protected-3'-nucleoside phosphoramidite |
| 4 | DMT | Activated 3'-nucleoside phosphoramidite |
| 5 | DMT | Phosphite triester ($P^{III}$) |
| 6* | Ac | L/SS or growing chain connected to L/SS |
| 7 | DMT | Phosphorothioate/ Phosphodiester; etc. ($P^V$) |

* represents structure of capped, uncoupled shortmer i = 3% $Cl_2CHCO_2H$ in $CH_2Cl_2$;
ii = $CH_3CN$ wash;
iii = 0.2 M solution of 3 / 0.45 M 1-$H$ tetrazole in $CH_3CN$;
iv = Oxidation
v = Capping reagents.
DMT = 4,4'-dimethoxy triphenylmethyl chloride;
L/SS: linker-solid-support;
B: T, $C^{Bz}$, $A^{Bz}$, or $G^{iBu}$

Figure 2

Preparation of DMT Amidite Reagent

Effluent from deprotection step containing orange-red DMT cation:

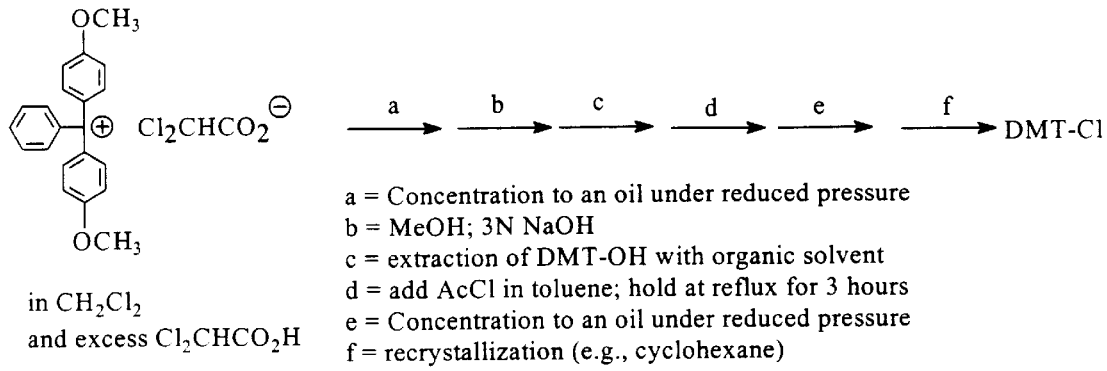

in $CH_2Cl_2$
and excess $Cl_2CHCO_2H$ $\xrightarrow{a} \xrightarrow{b} \xrightarrow{c} \xrightarrow{d} \xrightarrow{e} \xrightarrow{f}$ DMT-Cl a = Concentration to an oil under reduced pressure
b = MeOH; 3N NaOH
c = extraction of DMT-OH with organic solvent
d = add AcCl in toluene; hold at reflux for 3 hours
e = Concentration to an oil under reduced pressure
f = recrystallization (e.g., cyclohexane)

RECOVERY OF TRIARYLMETHYL HALIDE PROTECTING GROUPS CLEAVED DURING OLIGONUCLEOTIDE SYNTHESIS

FIELD OF THE INVENTION

The present invention is directed to methods for preparing triarylmethyl protecting group reagents. In preferred embodiments, the present invention provides methods for preparing protecting group reagents from products of oligonucleotide synthesis, preferably from waste products generated during cleavage of protecting groups during oligonucleotide synthesis.

BACKGROUND OF THE INVENTION

Modern therapeutic efforts are generally focused on the functions of proteins which contribute to many diseases in animals and man. There have been numerous attempts to modulate the production of such proteins by interfering with the function of biomolecules, such as intracellular RNA, that are involved in the synthesis of these proteins. It is anticipated that protein production will thus be inhibited or abolished, resulting in a beneficial therapeutic effect. The general object of such therapeutic approaches is to interfere with or modulate gene expression events that lead to the formation of undesired proteins.

One such method for the inhibition of specific gene expression is the use of oligonucleotides and oligonucleotide analogs as "antisense" drugs. These oligonucleotide or oligonucleotide analogs are designed to be complementary to a specific, target, messenger RNA (mRNA) or DNA, that encodes for the undesired protein. The oligonucleotide or oligonucleotide analog is expected to hybridize with good affinity and selectivity to its target nucleic acid, such that the normal essential functions of the target nucleic acid are disrupted. Antisense therapeutics hold great promise, as evidenced by the large number of oligonucleotides and oligonucleotide analogs that have been evaluated clinically in recent times. See generally, Ciba Foundation Symposium 209, *Oligonucleotides as Therapeutic Agents,* John Wiley & Sons, 1997. Further, oligonucleotides and oligonucleotide analogs have shown significant promise in the diagnosis of disease, and have also been used extensively as probes in diagnostic kits and as research reagents.

There is therefore a great need for the large scale production of oligonucleotides and oligonucleotide analogs for commercial application. The predominant synthetic regime currently in use for oligonucleotide synthesis is the phosphoramidite method, which is summarized in FIG. 1.

Briefly, oligonucleotides are synthesized on a solid-support via sequential reactions (shown as I-v in FIG. 1) in a predetermined order, typically controlled by a computerized pumping system. For example, synthesis typically begins with a nucleoside linked to a solid-support, typically via a linker molecule attached to the 3'-oxygen of the first nucleosidic synthon (as shown in FIG. 1, compound 1). Deprotection (or "cleavage") of the 5'-hydroxyl group is effected by treatment with deprotecting ("deblocking") solution I, 3% dichloroacetic acid (DCA) in dichloromethane, which removes the 5'—O—(4,4'-dimethoxytriphenylmethyl) hydroxyl protecting group to provide 2, having a free 5'—OH group. Such protecting groups are routinely used in oligonucleotide synthesis to allow selective reaction between two functional groups while protecting all other functionalities present in the reacting molecules.

Deprotection of the nucleoside 5'—O—DMT group as described above causes the release of a DMT cation (shown in FIG. 1), which has a characteristic bright red-orange color. Appearance of the colorful DMT cation facilitates monitoring of the coupling efficiency, and also is used by the computer system as a signal to discontinue the flow of 3% DCA deblocking solution.

Deprotection of triarylmethyl protecting groups such as DMT groups under acidic conditions is reported to be a reversible reaction. Therefore, removal of all of the DMT cation from the solid-support is crucial for the success of the deblocking step. Accordingly, in step ii the support is washed with dry solvent, typically acetonitrile (ACN), which removes traces of acidic solution and any trapped DMT-cation.

In step iii, a nucleoside phosphoramidite (3) is premixed with 1—H tetrazole to produce a very reactive P(III) tetrazolide intermediate (4) that reacts almost immediately with the 5'—OH group of (2) generating (5), which has a phosphite triester internucleosidic linkage. The unreacted excess (4) is then washed from the support with dry ACN.

The unstable P(III) species of (5) is then oxidized to a more stable P(V) internucleosidic linkage, such as a phosphodiester or phosphorothioate, to furnish a dimer or higher order support bound species, such as 7. A capping reaction (represented in FIG. 1 as Step v) is then performed to prevent unreacted 5'—OH groups from further extension. Typically, capping is performed with an acylating reagent. These steps are then repeated iteratively until the desired oligonucleotide is obtained. A more detailed treatment of oligonucleotide synthesis, and further representative synthetic procedures can be found in *Oligonucleotides And Analogues A Practical Approach,* Ekstein, F. Ed., IRL Press, N. Y, 1991, which incorporated herein in its entirety.

The preceding synthetic regime creates two large molecular weight waste products—one half mole excess of building block 4 (discarded in the process in ACN with 1—H tetrazole as an activator) and the triarylmethyl protecting group used for 5'—OH protection. The latter amounts to approximately 35% weight of the incoming monomeric phosphoramidite unit 3, and is released as triarylmethyl protecting group cation, typically in dichloromethane. Such triarylmethyl protecting groups are usually tailored molecules with distinct reactivity and stability to specific reaction conditions. Thus, they are expensive and add significantly to the cost of the synthetic process.

One critical challenge in the commercialization of oligonucleotide based therapeutic and diagnostic products is the ability to manufacture and market these products at a reasonable cost with minimal environmental impact. One solution to these problems is to minimize the waste of the nucleoside phosphoramidites used in the chemical syntheses. Thus, attempts have been made to recycle the excess unreacted amidite during synthesis of oligonucleotides. See for example Brill W., *Tetrahedron Letts.,* 1994, 35, 3041; Scremin et al., *J. Org. Chem.,* 1994, 59, 1963. However, these techniques have not been reported to have been successfully applied to the large-scale manufacture of oligonucleotides, as is required for research or commercial purposes.

It can be seen that there exists a need for synthetic methods that address the shortcomings of oligonucleotide synthesis discussed above. To date, there has been no report of the capture and use of protecting group cations generated during the deprotection of protected hydroxyl groups in oligonucleotide synthesis. The present invention is directed to this, as well as other, important ends.

SUMMARY OF THE INVENTION

The present invention provides novel methods for the preparation of triarylmethyl protecting group reagents.

In preferred embodiments, the triarylmethyl protecting group reagents are prepared from a by-product of standard oligonucleotide synthetic reactions.

In some preferred embodiments, synthetic methods are provided comprising:

providing a monomeric or oligomeric nucleobase bearing compound having a hydroxyl group, the hydroxyl group being protected with a triarylmethyl protecting group;

treating the compound with a deprotecting reagent to produce a free triarylmethyl protecting group;

contacting the free triarylmethyl protecting group with a base to form a triarylmethyl alcohol; and reacting the triarylmethyl alcohol with a halide reagent to form a triarylmethyl halide protecting reagent.

In some preferred embodiments, the triarylmethyl halide protecting reagent has the Formula:

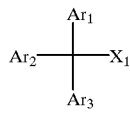

wherein:

$X_1$ is Cl, Br or I; and each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

In more preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred.

Preferably, the base is sodium hydroxide, potassium hydroxide, lithium hydroxide or barium hydroxide, with sodium hydroxide being more preferred.

In some preferred embodiments, the halide reagent is acetyl chloride, acetyl bromide, acetyl iodide, thionyl chloride, thionyl bromide, phosphorus trichloride, phosphorus tribromide, phosphorus oxychloride, or carbon tetrabromide, with acetyl chloride being more preferred.

In further preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl .(TBTr), 4,4',4"-tris(4,5-dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred; the base is sodium hydroxide, potassium hydroxide, lithium hydroxide or barium hydroxide, with sodium hydroxide being more preferred; and the halide reagent is acetyl chloride, acetyl bromide, acetyl iodide, thionyl chloride, thionyl bromide, phosphorus trichloride, phosphorus tribromide, phosphorus oxychloride, or carbon tetrabromide, with acetyl chloride being more preferred.

In further preferred embodiments, the contacting of the free triarylmethyl protecting group with the base is performed in a water-miscible organic solvent, which is preferably methanol, ethanol, propanol, acetonitrile, or tetrahydrofuran, with methanol being more preferred.

In still further preferred embodiments, the triarylmethyl alcohol is reacted with the halide reagent in a water-immiscible solvent, which is preferably diethyl ether, diisopropyl ether, ethyl acetate, dichloromethane, chloroform, or toluene, with toluene being more preferred.

The present invention also provides synthetic methods comprising:

providing a monomeric or oligomeric nucleobase bearing compound having a hydroxyl group, the hydroxyl group being protected with a triarylmethyl protecting group;

treating the compound with a deprotecting reagent to produce a free triarylmethyl protecting group;

contacting the free triarylmethyl protecting group with a base to form a triarylmethyl alcohol; and reacting the triarylmethyl alcohol with a tetrahaloborate reagent to form a triarylmethyl teterahaloborate protecting reagent.

Preferably, the triarylmethyl teterahaloborate protecting reagent has the Formula:

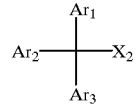

wherein:

$X_2$ is a tetrahaloborate; and each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, and pyrenyl; or Ar₁ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, or pyrenyl; or Ar₂ and Ar₃ together form xanthanen-9-yl or thioxanthen-9-yl.

More preferably, the tetrahaloborate is trityl, monomethoxytrityl (MMTr), 4,4'-dimethoxytrityl (DMTr), 4,4',4"-trimethoxytrityl (TMTr), 4,4',4"-tris-(benzoyloxy) trityl (TBTr), 4,4',4"-tris(4,5 -dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred.

In some prefrerred embodiments, the base is sodium hydroxide, potassium hydroxide, lithium hydroxide or barium hydroxide, with sodium hydroxide being preferred.

In some preferred embodiments, the tetrahaloborate reagent is tetrafluoroboric acid in acetic anhydride.

In more preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred; the base is sodium hydroxide, potassium hydroxide, lithium hydroxide or barium hydroxide, with sodium hydroxide being more preferred; and the tetrahaloborate reagent is tetrafluoroboric acid in acetic anhydride.

Also provided in accordance with the present invention are methods for the preparation of a triarylmethyl halide or tetrahaloborate protecting reagent having the Formula:

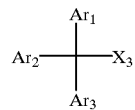

wherein:

X₃ is Cl, Br, I, or tetrahaloboronyl; and each of Ar₁, Ar₂, and Ar₃ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, and pyrenyl; or Ar₁ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3, 5-hexadienoxy)-phenyl, 4-(4,5-dichlorophthalimido) phenyl, napthyl, anthracenyl, or pyrenyl; or Ar₂ and Ar₃ together form xanthanen-9-yl or thioxanthen-9-yl;

comprising the steps of:

cleaving a triarylmethyl protecting group during the course of oligonucleotide synthesis;

collecting the effluent from the cleavage, the effluent containing free triarylmethyl protecting group;

contacting the free triarylmethyl protecting group with a base to form a triarylmethyl alcohol; and reacting the triarylmethyl alcohol with
  a) a halide reagent to form the triarylmethyl halide protecting reagent; or
  b) a tetrahaloborate reagent to form the triarylmethyl teterahaloborate protecting reagent.

In some preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being preferred.

In further preferred embodiments, the base is sodium hydroxide, potassium hydroxide, lithium hydroxide or barium hydroxide, with sodium hydroxide being preferred.

In more preferred embodiments, the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5- dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl with 4,4'-dimethoxytrityl being more preferred; the base is sodium hydroxide, potassium hydroxide, lithium hydroxide or barium hydroxide, with sodium hydroxide being more preferred; and the tetrahaloborate reagent is tetrafluoroboric acid in acetic anhydride.

In some preferred embodiments, the contacting of the free triarylmethyl protecting group with the base is performed in a water-miscible organic solvent, which is preferably methanol, ethanol, propanol, acetonitrile, or tetrahydrofuran, with methanol being more prefreered.

In some especially preferred embodiments of the foregoing methods, the triarylmethyl protecting group is 4,4'-dimethoxytrityl, the base is sodium hydroxide, and the halide reagent is acetyl chloride.

BRIEF DESCRIPTION OF THE DRAWINGS

FIG. 1 shows a typical solid state oligonucleotide synthetic protocol.

FIG. 2 shows the preparation of amidite DMT reagent according to some preferred embodiments of the invention.

DETAILED DESCRIPTION OF THE PREFERRED EMBODIMENTS

The present invention presents novel methods for preparing triarylmethyl protecting group reagents, preferably from by-products of oligonucleotide synthesis reactions.

In some preferred embodiments, the methods of the invention comprise:

providing a monomeric or oligomeric nucleobase bearing compound having a hydroxyl group, the hydroxyl group being protected with a triarylmethyl protecting group;

treating the compound with a deprotecting reagent to produce a free triarylmethyl protecting group;

contacting the free triarylmethyl protecting group with a base to form a triarylmethyl alcohol; and reacting the triarylmethyl alcohol with a halide reagent to form a triarylmethyl halide protecting reagent.

In some preferred embodiments, the triarylmethyl halide protecting reagent has the Formula:

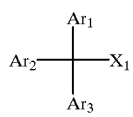

wherein:

$X_1$ is Cl, Br or I; and each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido)phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

More preferred $Ar_1$, $Ar_2$, and $Ar_3$ groups include trityl, monomethoxytrityl (MMTr), 4,4'-dimethoxytrityl (DMTr), 4,4',4"-trimethoxytrityl (TMTr), 4,4',4"-tris-(benzoyloxy) trityl (TBTr), 4,4',4"-tris(4,5-dichlorophthalimido)trityl (CPTr), 4,4',4"-tris-(levulinyloxy)trityl (TLTr), p-anisyl-1-naphthyl-phenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl, with 4,4'-dimethoxytrityl being more preferred.

Although the foregoing represents preferred embodiments of the methods of the invention, it will be appreciated that a large number of diverse members of this class of protecting groups are available and have been widely used in the art. Variations in the structure of trityl protecting groups have been designed to optimize or provide ease of protection and cleavage reactions, and alteration of the physicochemical properties of the monomers and oligonucleotides. The methods of the present invention find applicability in the preparation of such protecting groups.

The present invention affords significant advantages in the performance of oligonucleotide synthesis. For example, in accordance with the methods of the invention, the amount of waste generated at the deprotecting stage of oligonucleotide synthesis can be significantly reduced. Thus, the methods of the invention also provide oligonucleotide synthesis at reduced cost, and with a significantly lower ecological burden.

The methods of the present invention are useful for the preparation of a wide variety of protecting group reagents that are in turn useful for the protection of hydroxyl groups, and in particular 5'-hydroxy groups of nucleoside building blocks used in oligonucleotide synthesis. In accordance with the preferred embodiments of the methods of the invention, a monomeric or oligomeric nucleobase bearing compound having a hydroxyl group protected with a triarylmethyl protecting group is treated with a deprotecting reagent to produce a free triarylmethyl protecting group. In preferred embodiments, the monomeric or oligomeric nucleobase bearing compound is the growing nucleotide chain in standard oligonucleotide synthesis, which is optionally attached to a solid support. As used herein, the term "treating the compound with a deprotection reagent" means bringing the compound and the deprotecting reagent into sufficient proximity such that the deprotection reaction occurs.

Depending on the nature of the purification strategy to be used, the 5'-protecting group on the terminal nucleoside unit of the oligonucleotide can be cleaved during the synthesis process (e.g., when ion-exchange purification may be desired) or cleaved post-synthesis (e.g., after reverse-phase purification of the oligonucleotide).

Deprotecting reagents useful in the methods of the invention include those known to be effective for removal of 5'-hydroxyl protecting groups. In some preferred methods of the present invention, cleavage is preferably performed under acidic conditions using a protic or Lewis acid in an organic solvent. Suitable organic solvents include dichloromethane, chloroform, carbon tetrachloride, toluene, xylene, acetonitrile and tetrahydrofuran. In addition to acidic deprotection protocols, deprotection protocols which avoid acidic conditions are also amenable to the present invention. Such protocols are advantageous in that they ameliorate the problems of depurination in purine rich oligonucleotides, occasionally seen with acidic deprotection. For example, the use of naphthalene radical anions in HMPT to effect cleavage of 5'—O—MMTr groups has been reported and used for solution phase oligonucleotide synthesis. See Greene and Letsinger, *Tetrahedron Lett.*, 1975, 2081; Letsinger and Finnan, *J. Am. Chem. Soc.*, 1975, 97, 7197. Boron trifluoride etherate in dichloromethane also has been reported as useful for the cleavage of 5'—O—trityl protecting groups. See Engels, *Angew. Chem. Int. Ed. Engl.*, 1979, 18, 148. A milder Lewis acid such as zinc bromide in nitromethane or dichloromethane also has been used to cleave triarylmethyl protecting groups during solid phase oligonucleotide synthesis. See Matteucci and Caruthers, *Tetrahedron Lett.*, 1980, 21, 3243; Kohli et al., *Tetrahedron Lett.*, 1980, 21, 2683. Tetra-n-butyl ammonium peroxydisulfate has been found to be a good deprotecting reagent for the removal of trityl protecting groups. Cleavage of 5'—O—DMTr groups from nucleosides has been reported in excellent yields, under neutral and mild conditions without concomitant cleavage of the glycosidic bond. See Yang et al., *Heteroatom Chem.*, 1997, 8, 435. Quantitative cleavage of trityl ethers may also be accomplished using ferric chloride hexahydrate in dichloromethane, at room temperature, without affecting other protecting groups that may be present in the molecule. See Ding et al., *Carbohydrate Res.*, 1997, 303, 445. Other representative protecting groups and deprotecting reagents can be found, for example, in Greene and Wuts, *Protective Groups in Organic Synthesis*, 2d ed., John Wiley & Sons, New York, 1991, which is incorporated by reference in its entirety, and in Ekstein, supra. Each of the foregoing cleavage protocols, as well as others, are amenable to the methods of the invention.

In some preferred embodiments of the methods of the invention, each time a 5' protecting group is cleaved during oligonucleotide synthesis, the reaction effluent containing the protecting group cation product of the cleavage step is collected. The collection procedure can be modified, if desired, to allow for particular aspects of the synthesis, for example where some of the nucleobase synthons bear 5'-protecting groups that are different from those used for the construction of the remainder of the oligonucleotide.

In some preferred embodiments of the present invention, the organic solvent contained in the effluent is evaporated to yield a residue of the triarylmethyl cation. In some preferred embodiments, this residue is dissolved in a water-miscible organic solvent, which is preferably methanol, ethanol, propanol, acetonitrile or tetrahydrofuran, with methanol being more preferable.

The solution of the triarylmethyl cations is subsequently contacted with excess base to form the alcohol of the triarylmethyl protecting group. Contacting of the triarylmethyl cation and base can be accomplished, for example, by adding a base solution to a solution of the cation. Representative bases useful for this purpose include aqueous sodium hydroxide, potassium hydroxide, lithium hydroxide or barium hydroxide, with 3 N sodium hydroxide being more preferable.

In some preferred embodiments of the present invention, the alcohol of the protecting group is extracted with a water-immiscible solvent to form a solution. Suitable water-immiscible solvents include, for example, diethyl ether, diisopropyl ether, ethyl acetate, dichloromethane, chloroform, and toluene, with toluene being more preferable.

According to the some preferred embodiments of the methods of the present invention, the solution containing the alcohol is reacted with a halide reagent to form the triarylmethyl protecting group reagent. Preferably, the halide reagent is in excess. As used herein, the term "reacting the triarylmethyl alcohol with a halide reagent" means placing the triarylmethyl alcohol together with the halide reagent for a time and under conditions of temperature and pressure such that the triarylmethyl protecting group reagent is formed. In some preferred embodiments, the alcohol is heated together with the halide reagent. Preferably, the alcohol is placed together with the halide reagent and held at reflux, for a period of time sufficient to form the triarylmethyl protecting group reagent, typically for about 1 to about 3 hours. Suitable halide reagents include, for example, acetyl chloride, acetyl bromide, acetyl iodide, thionyl chloride, thionyl bromide, phosphorus trichloride, phosphorus tribromide, phosphorus oxychloride, and carbon tetrabromide.

In some preferred embodiments, the water-immiscible solvent is evaporated to form a residue of triarylmethyl protecting group reagent, which can then be purified by any of a variety of standard purification techniques to afford the purified product. In some preferred embodiments, the purification is achieved by recrystalization from a suitable recrystalization solvent, for example pentane, hexane, cyclopentane, cyclohexane, cycloheptane, or toluene.

In some preferred embodiments, the triarylmethyl alcohol is reacted with a tetrahaloborate reagent to form a triarylmethyl teterahaloborate protecting reagent. In particularly preferred embodiments, the tetrahaloborate reagent is tetrafluoroborate, preferably in acetic anhydride. In preferred embodiments, the triarylmethyl teterahaloborate protecting reagent has the Formula:

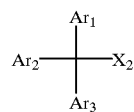

wherein:

X$_2$ is a tetrahaloborate; and Ar$_1$, Ar$_2$, and Ar$_3$ are as described above.

Also provided in accordance with the present invention are methods for the preparation of a triarylmethyl halide or tetrahaloborate protecting reagent having the Formula:

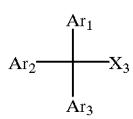

wherein:
X₃ is Cl, Br, I, or a tetrahaloborate; and Ar₁, Ar₂, and Ar₃ are as defined above, comprising the steps of:
cleaving a triarylmethyl protecting group during the course of oligonucleotide synthesis;
collecting the effluent from the cleavage, the effluent containing free triarylmethyl protecting group;
contacting the free triarylmethyl protecting group with a base to form a triarylmethyl alcohol; and
reacting the triarylmethyl alcohol with
  a) a halide reagent to form the triarylmethyl halide protecting reagent; or
  b) a tetrahaloborate reagent to form the triarylmethyl teterahaloborate protecting reagent.

In some preferred embodiments, the triarylmethyl protecting group is cleaved during the course of oligonucleotide synthesis according to the phosphoramidite method.

In the context of the present invention, the term "oligonucleotide" refers to a plurality of joined nucleotide units formed in a specific sequence. The term nucleotide has its accustomed meaning as the phosphoryl ester of a nucleoside. The term "nucleoside" also has its accustomed meaning as a pentofuranosyl sugar which is bound to a nucleosidic base (i.e., a nitrogenous heterocyclic base or "nucleobase").

It will be appreciated that the methods of the present invention can be applied to the synthesis of oligonucleotides by a number of different chemical approaches such as phosphoramidite, phosphotriester and phosphonate chemistries and by solution or solid phase reactions, as has been widely reported in the literature. The nucleotide building blocks and therefore the oligonucleotides synthesized using the methods of this invention may have both naturally occurring and non-naturally occurring constituent sugars, internucleoside linkages and/or nucleobases. Non-naturally occurring sugars, internucleoside linkages and nucleobases are typically structurally distinguishable from, yet functionally interchangeable with, naturally occurring sugars (e.g. ribose and deoxyribose), internucleoside linkages (i.e. phosphodiester linkages), and nucleosidic bases (e.g., adenine, guanine, cytosine, thymine). Thus, non-naturally occurring moieties include all such structures which mimic the structure and/or function of naturally occurring moieties, and which aid in the binding of the oligonucleotide analog to a target, or otherwise advantageously contribute to the properties of the synthesized oligonucleotide.

Representative examples of non-naturally occurring sugars include sugars having any of a variety of substituents attached to their any one or more positions on the sugar. These include 2'-substitutions such as, for example, halides, O-alkyl, O-aminoalkyl, O-alkyloxyalkyl, -protected O-aminoalkyl, O-alkylaminoalkyl, O-dialkylaminoalkyl, O-imidazolylalkyl, O-dialkylaminooxyalkyl, O-alkylaminooxyalkyl, and polyethers of the formula (O-alkyl)m, where m is 1 to about 10.

Preferred among these polyethers are linear and cyclic polyethylene glycols (PEGs), and (PEG)-containing groups such as crown ethers and those which are disclosed by Ouchi et al., *Drug Design and Discovery*, 1992, 9, 93, Ravasio et al., *J. Org. Chem.*, 1991, 56, 4329, and Delgardo et al., *Critical Reviews in Therapeutic Drug Carrier Systems*, 1992, 9, 249. Further sugar modifications are disclosed in Cook, *Anti-Cancer Drug Design*, 1991, 6, 585, Cook, Medicinal Chemistry Strategies for Antisense Research, in *Antisense Research and Applications*, Crooke et al., CRC Press Inc., Boca Raton, Fla., 1993. O-Fluoro, O-alkyl, O-aminoalkyl, O-imidazolylalkyl, O-alkylaminoalkyl, and O-aminoalkyl 2'-substitutions are described in U.S. patent application Ser. No. 08/398,901, filed Mar. 6, 1995, entitled Oligomeric Compounds having Pyrimidine Nucleotide(s) with 2' and 5 Substitutions, the disclosure of which is hereby incorporated by reference.

Oligonucleotides bearing sugars having O-substitutions on the ribosyl ring are also amenable to the present invention. Representative substitutions for ring O include S, $CH_2$, CHF, and $CF_2$, see, e.g., Sanghvi and Cook in Carbohydrate Modifications in Antisense Research, ACS Symposium Series 580, ACS Publication, Washington, DC, 1994.

Representative nucleobases that may be present in the building blocks and oligonucleotides used in the methods of this invention include, adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-aza uracil, cytosine and thymine, 5-uracil (pseudo uracil), 4-thiouracil, 8-halo, oxa, amino, thio, thioalkyl, hydroxyl and other 8-substituted adenines and guanines, 5-trifluoromethyl and other 5-substituted uracils and cytosines, and 7-methylguanine. Further naturally and non-naturally occurring nucleobases include those disclosed by Metrigan et al. in U.S. Pat. No., 3,687,808, by Sanghvi, in Chapter 15, *Antisense Research and Applications*, Ed. S. T. Crooke and B. Lebleu, CRC Press, Boca Raton, Fla., 1993, by Englisch et al., *Angewandte Chemie, Int. Ed.,* 1991, 30, 613, in *The Concise Encyclopedia of Polymer Science and Engineering,* Ed. J. I. Kroschwitz, John Wiley and Sons, 1990, pp.858–859, and by Cook, *Anti-Cancer Drug Design,* 1991, 6, 585. The disclosures of each of the foregoing is incorporated by reference in their entirety. The terms 'nucleosidic base' and 'nucleobase' are further intended to include heterocyclic compounds that can serve as nucleosidic bases, including certain 'universal bases' that are not nucleosidic bases in the most classical sense, but function similarly to nucleosidic bases. One representative example of such a universal base is 3-nitropyrrole.

Representative internucleotide linkages that may be present in the oligonucleotides include, but are not limited to, phosphodiester, phosphorothioate, phosphoroselenoate, phosphorodithioate, H-phosphonate, methyl phosphonate, and alkyl phosphonate. These linkages may be between the 5'—O one nucleotide unit and any one of the 2'-, 3'-, or 4'-positions of another nucleotide unit. See generally, Sanghvi in "DNA with Altered Backbones in Antisense Applications" in Comprehensive Organic Natural Product Chemistry, Vol. 7, Elservier Science Ltd., Oxford, 1998, which is hereby incorporated by reference in its entirety.

Additional advantages and novel features of this invention will become apparent to those skilled in the art upon examination of the examples thereof provided below, which should not be construed as limiting the appended claims.

EXAMPLE 1

A 60 mmole scale synthesis of oligonucleotide was commenced on a Pharmacia OligoProcess instrument. Deprotection of the 5'-protecting groups during this synthesis was performed using a 3% solution of dichloroacetic acid in dichloromethane. The waste stream generated from the cleavage of the 5'—O-dimethoxytrityl protecting groups during the deblocking cycles (FIG. 1, step I) was collected manually (12 L of 3% DCA in DCM containing trityl cation). The solution was concentrated under vacuum (FIG. 2, step a)to remove most of the dichloromethane. The oily-red residue was then dissolved in MeOH (1.8 L) and NaOH (aqueous, 3 N, 1.5 L) was added over a period of 1 hour followed by stirring for 16 hours ambient temperature (FIG. 2, step b). The reaction mixture was concentrated under vacuum to remove most of the MeOH. The remaining aqueous layer was extracted with toluene (200 mL ×3) (FIG. 2, step c) and the organic phases were combined, and dried ($Na_2SO_4$). A small sample (50 mL) of the toluene solution was evaporated to give 4,4'-dimethoxytrityl alcohol (DMT—OH in FIG. 1). The compound was verified by mass spectrometry: MS (FAB) m/z 343 ($MNa^+$)

The toluene solution was then concentrated to a minimum volume (~80 mL). Acetylchloride (8.5 mL, 9.42 g, 0.12 mol) was added and the solution was refluxed for 2 hours under argon (FIG. 1, step d). Reaction mixture was then cooled to room temperature, and the solution was concentrated under vacuum (FIG. 2, step e). Cyclohexane (100 mL) was added to the residue and the mixture was allowed to stand in a refrigerator for 16 hours. The crystallized material filtered, washed with cold cyclohexane (50 mL×2) and dried under reduced vacuum to furnish DMT—Cl (17.5 g, 89.7%). m.p. 122–124° C. [Rathore et al., Indian J. Chem. 34B (1995) 634–635: 119–123° C.] $^1H$ NMR (200 MHZ, $CDCl_3$) d 3.84 (s, 6H) , 6.87 (d, 4H) , 7.20–7.36 (m, 9H) $^{13}C$ NMR (50 MHZ, $CDCl_3$) d 55.37, 82.15, 113.02, 127.76, 129.76, 131.09, 137.85, 145.84, 159.09. Anal. Calcd. for $C_{21}H_{19}ClO_2$ (338.83): C, 74.44; H, 5.65. Found: C, 74.66; H, 5.82. The identity of recaptured DMT—Cl was further confirmed by TLC cospotting with an authentic sample in three different solvents ($CH_2Cl_2$: $R_f$ 0.25; $CH_3CN$: $R_f$ 0.9; 30% EtOAc in Hexanes: $R_f$ 0.4). In addition, this DMT—Cl was also used for the preparation of 5'—O—DMT protected nucleosides and the m.p., $^1H$ and $^{13}C$ NMR, and C, H, and N analyses were identical to literature values for the given compounds.

EXAMPLE 2

A 60 mmole scale synthesis of oligonucleotide is commenced as in Example 1. Deprotection of the 5'-protecting groups during this synthesis is performed using a 3% solution of dichloroacetic acid in dichloromethane. The waste stream generated from the cleavage of the 5'—O-dimethoxytrityl protecting groups during the deblocking cycles is collected manually (12 L of 3% DCA in DCM containing trityl cation). The solution is concentrated under vacuum to remove most of the dichloromethane. The oily-red residue is then dissolved in MeOH (1.8 L) and NaOH (aqueous, 3 N, 1.5 L) is added over a period of 1 hour followed by stirring for 16 hours ambient temperature. The reaction mixture is concentrated under vacuum to remove most of the MeOH. The remaining aqueous layer is extracted with toluene (200 mL×3) (FIG. 2, step c) and the organic phases are combined, and dried ($Na_2SO_4$). The toluene solution is then concentrated to a minimum volume (~80 mL).

The 4,4'-dimethoxytrityl alcohol is then converted to the 4,4'-dimethoxytrityl tetrafloroborate according to the procedure of Bleasdale, C. et al., J. Chem. Soc. Perkin Trans. 1:803–805 (1990). The 4,4'-dimethoxytrityl alcohol is dissolved in 20 molar equivalents of warm acetic anhydride. The solution is allowed to cool, and 40% auqeous tetrafluoroboric acid (4–5 molar equivalents) is added at a rate sufficient to ensure that the temperature does not rise above 25° C., forming a dark red solution. Addition of ether to the solution yields the product as deep orange crystals.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the present invention, and that such changes and modifications may be made without departing from the spirit of the invention. It is, therefore, intended that the appended claims cover all such equivalent variations as fall within the true spirit and scope of the invention.

FIG. 1

Solid Phase Oligonucleotide Synthesis

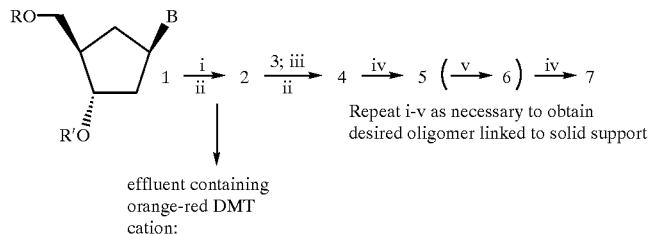

effluent containing
orange-red DMT
cation:

Repeat i-v as necessary to obtain
desired oligomer linked to solid support

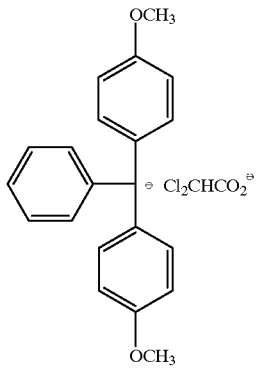

in CH₂Cl₂
and excess Cl₂CHCO₂H

|   | R   | R'                                              |                                                                     |
|---|-----|-------------------------------------------------|---------------------------------------------------------------------|
| 1 | DMT | L/SS                                            | i = 3% Cl₂CHCO₂H in CH₂Cl₂;                                         |
| 2 | H   | L/SS                                            | ii = CH₃CN wash;                                                    |
| 3 | DMT | 5'-Protected-3'-nucleoside phosphoramidite      | iii 0.2 M solution of 3/0.45 M 1-H tetrazole in CH₃CN;              |
| 4 | DMT | Activated 3'-nucleoside phosphoramidite         | iv = Oxidation                                                       |
| 5 | DMT | Phosphite triester (P$^{III}$)                  | v = Capping reagents.                                                |
| 6*| Ac  | L/SS or growing chain connected to L/SS         | DMT = 4,4'-dimethoxy triphenylmethyl chloride; L/SS: linker-solid-support; |
| 7 | DMT | Phosphorothioate/Phosphodiester; etc. (P$^V$)  | B: T, C$^{Bz}$, A$^{Bz}$, or G$^{iBu}$                               |

*represents structure of capped, uncoupled shortmer

FIG. 2
Preparation of DMT Amidite Reagent

Effluent from deprotection step containing orange-red DMT cation:

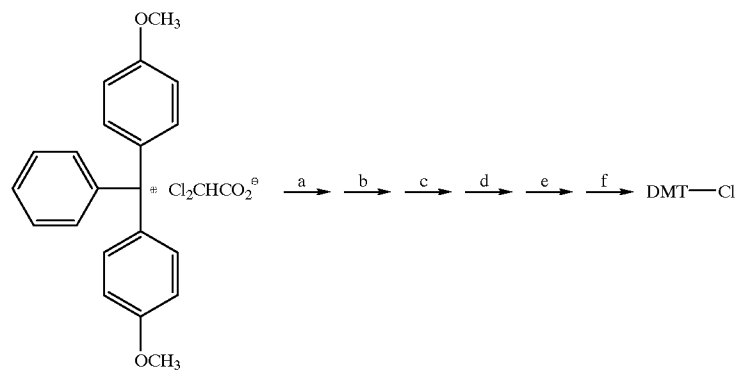

in CH₂Cl₂
and excess Cl₂CHCO₂H a = Concentration to an oil under reduced pressure
b = MeOH; 3N NaOH
c = extraction of DMT-OH with organic solvent
d = add AcCl in toluene; hold at reflux for 3 hours
e = Concentration to an oil under reduced pressure
f = recrystallization (e.g., cyclohexane)

What is claimed is:

1. A synthetic method comprising:
providing a monomeric or oligomeric nucleobase bearing compound having a hydroxyl group, the hydroxyl group being protected with a triarylmethyl protecting group;
treating the compound with a deprotecting reagent to produce a free triarylmethyl protecting group;
contacting the free triarylmethyl protecting group with a base to form a triarylmethyl alcohol; and
reacting the triarylmethyl alcohol with a halide reagent to form a triarylmethyl halide protecting reagent.

2. The method of claim 1 wherein the triarylmethyl halide protecting reagent has the Formula:

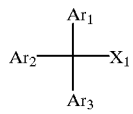

wherein:
X is Cl, Br or I; and
each of $Ar_1$, $Ar_2$, and $Ar_3$ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or $Ar_1$ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or $Ar_2$ and $Ar_3$ together form xanthanen-9-yl or thioxanthen-9-yl.

3. The method of claim 2, wherein the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl.

4. The method of claim 3, wherein the triarylmethyl protecting group is 4,4'-dimethoxytrityl.

5. The method of claim 1 wherein the base is sodium hydroxide, potassium hydroxide, lithium hydroxide or barium hydroxide.

6. The method of claim 5, wherein the base is sodium hydroxide.

7. The method of claim 1 wherein the halide reagent is acetyl chloride, acetyl bromide, acetyl iodide, thionyl chloride, thionyl bromide, phosphorus trichloride, phosphorus tribromide, phosphorus oxychloride, or carbon tetrabromide.

8. The method of claim 7, wherein the halide reagent is acetyl chloride.

9. The method of claim 1, wherein the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl;
the base is sodium hydroxide, potassium hydroxide, lithium hydroxide or barium hydroxide; and
the halide reagent is acetyl chloride, acetyl bromide, acetyl iodide, thionyl chloride, thionyl bromide, phosphorus trichloride, phosphorus tribromide, phosphorus oxychloride, or carbon tetrabromide.

10. The method of claim 9 wherein the triarylmethyl protecting group is 4,4'-dimethoxytrityl.

11. The method of claim 9 wherein the base is sodium hydroxide.

12. The method of claim 9 wherein the halide reagent is acetyl chloride.

13. The method of claim 1 wherein the triarylmethyl protecting group is 4,4'-dimethoxytrityl; the base is sodium hydroxide; and the halide reagent is acetyl chloride.

14. The method of claim 1 wherein the reaction of the free triarylmethyl protecting group with the base is performed in a water-miscible organic solvent.

15. The method of claim 14 wherein the solvent is methanol, ethanol, propanol, acetonitrile, or tetrahydrofuran.

16. The method of claim 1 wherein the triarylmethyl alcohol is contacted with the halide reagent in a water-immiscible solvent.

17. The method of claim 16 wherein the water-immiscible solvent is diethyl ether, diisopropyl ether, ethyl acetate, dichloromethane, chloroform, or toluene.

18. A synthetic method comprising:
providing a monomeric or oligomeric nucleobase bearing compound having a hydroxyl group, the hydroxyl group being protected with a triarylmethyl protecting group;
treating the compound with a deprotecting reagent to produce a free triarylmethyl protecting group;
contacting the free triarylmethyl protecting group with a base to form a triarylmethyl alcohol; and
reacting the triarylmethyl alcohol with a tetrahaloborate reagent to form a triarylmethyl teterahaloborate protecting reagent.

19. The method of claim 18 wherein the triarylmethyl teterahaloborate protecting reagent has the Formula:

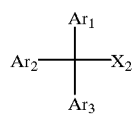

wherein:

X₂ is a tetrahaloborate; and each of Ar₁, Ar₂, and Ar₃ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or Ar₁ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or Ar₂ and Ar₃ together form xanthanen-9-yl or thioxanthen-9-yl.

20. The method of claim 19, wherein the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl.

21. The method of claim 20, wherein the triarylmethyl protecting group is 4,4'-dimethoxytrityl.

22. The method of claim 18 wherein the base is sodium hydroxide, potassium hydroxide, lithium hydroxide or barium hydroxide.

23. The method of claim 22, wherein the base is sodium hydroxide.

24. The method of claim 18 wherein the tetrahaloborate reagent is tetrafluoroboric acid in acetic anhydride.

25. The method of claim 18, wherein the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr), or 4,4'-di-3,5-hexadienoxytrityl;

the base is sodium hydroxide, potassium hydroxide, lithium hydroxide or barium hydroxide; and the tetrahaloborate reagent is tetrafluoroboric acid in acetic anhydride.

26. The method of claim 25 wherein the triarylmethyl protecting group is 4,4'-dimethoxytrityl.

27. The method of claim 25 wherein the base is sodium hydroxide.

28. The method of claim 18 wherein the triarylmethyl protecting group is 4,4'-dimethoxytrityl; the base is sodium hydroxide; and the tetrahaloborate reagent is tetrafluoroboric acid in acetic anhydride.

29. A method for the preparation of a triarylmethyl halide or tetrahaloborate protecting reagent having the Formula:

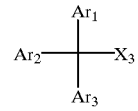

wherein:

X₃ is Cl, Br, I, or a tetrahaloborate; and each of Ar₁, Ar₂, and Ar₃ is independently phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, and pyrenyl; or Ar₁ is selected from a group consisting of phenyl, 2-methoxyphenyl, 3-methoxyphenyl, 4-methoxyphenyl, 2,4-dimethoxyphenyl, 3,4-dimethoxyphenyl, 3,4-methylenedioxy-phenyl, 4-butylphenyl, 4-tert-butyl-phenyl, 4-biphenylyl, 4-chlorophenyl, 4-fluorophenyl, 4-nitrophenyl, 2-furyl, 4-benzoyloxyphenyl, 4-levulinyloxy-phenyl, 3-imidazolylmethyl-phenyl, 4-decyloxy-phenyl, 4-hexadecyloxy-phenyl, 4-octadecyloxy-phenyl, 4-(3,5-hexadienoxy)-phenyl, 4-(4,5-dichlorophthalimido) phenyl, napthyl, anthracenyl, or pyrenyl; or Ar₂ and Ar₃ together form xanthanen-9-yl or thioxanthen-9-yl;

comprising the steps of:

cleaving a triarylmethyl protecting group during the course of oligonucleotide synthesis;

collecting the effluent from the cleavage, the effluent containing free triarylmethyl protecting group;

contacting the free triarylmethyl protecting group with a base to form a triarylmethyl alcohol; and reacting the triarylmethyl alcohol with a) a halide reagent to form the triarylmethyl halide protecting reagent; or b) a tetrahaloborate reagent to form the triarylmethyl teterahaloborate protecting reagent.

30. The method of claim 31, wherein the triarylmethyl protecting group is trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy) trityl (TLTr), p-anisyl-1-naphthylphenylmethyl, di-o-anisyl- 1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4''-tris-(tert-butylphenyl)methyl (TTTr), or 4,4'-di-3,5-hexadienoxytrityl.

31. The method of claim 30, wherein the triarylmethyl protecting group is 4,4'-dimethoxytrityl.

32. The method of claim 30 wherein the base is sodium hydroxide, potassium hydroxide, lithium hydroxide or barium hydroxide.

33. The method of claim 32, wherein the base is sodium hydroxide.

34. The method of claim 29, wherein the triarylmethyl protecting group is trityl, monomethoxytrityl (MMTr), 4,4'-dimethoxytrityl (DMTr), 4,4',4''-trimethoxytrityl (TMTr), 4,4',4''-tris-(benzoyloxy)trityl (TBTr), 4,4',4''-tris(4,5-dichlorophthalimido)trityl (CPTr), 4,4',4''-tris(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4''-tris-(tert-butylphenyl)methyl (TTTr), or 4,4'-di-3,5-hexadienoxytrityl;

the base is sodium hydroxide, potassium hydroxide, lithium hydroxide or barium hydroxide; and the tetrahaloborate reagent is tetrafluoroboric acid in acetic anhydride.

35. The method of claim 34 wherein the triarylmethyl protecting group is 4,4'-dimethoxytrityl.

36. The method of claim 34 wherein the base is sodium hydroxide.

37. The method of claim 34 wherein the triarylmethyl protecting group is 4,4'-dimethoxytrityl; and the base is sodium hydroxide.

38. The method of claim 31 wherein the reaction of the free triarylmethyl protecting group with the base is performed in a water-miscible organic solvent.

39. The method of claim 33 wherein the solvent is methanol, ethanol, propanol, acetonitrile, or tetrahydrofuran.

* * * * *

UNITED STATES PATENT AND TRADEMARK OFFICE
CERTIFICATE OF CORRECTION

PATENT NO. : 6,124,484
DATED : September 26, 2000
INVENTOR(S) : Sanghvi et al.

It is certified that error appears in the above-identified patent and that said Letters Patent is hereby corrected as shown below:

Column 4,
Lines 50 and 52, please delete "teterahaloborate" and insert therefor
-- tetrahaloborate --.

Column 6,
Line 53, please delete "p-tolyldipheylmethyl" and insert therefor
-- p-tolyldiphenylmethyl --

Column 10,
Lines 49 and 52, please delete "teterahaloborate" and insert therefor
-- tetrahaloborate --.

Column 11,
Line 21, please delete "teterahaloborate" and insert therefor -- tetrahaloborate --.
Line 62, please delete "(O-alkyl)m" and insert therefor -- $(O\text{-}alkyl)_m$ --.

Column 17,
Line 4, please delete "p-tolydipheylmethyl" and insert therefor
-- p-tolyldiphenylmethyl --.
Line 53, please delete "p-tolyldipheylmethyl" and insert therefor
-- p-tolyldiphenylmethyl --.

Column 18,
Line 15, please delete "p-tolyldipheylmethyl" and insert therefor -- p-tolyldiphenylmethyl --.
Lines 64 and 67, please delete "teterahaloborate" and insert therefor
-- tetrahaloborate --.

Column 19,
Lines 39 and 62, please delete "p-tolyldipheylmethyl" and insert therefor -- p-tolyldiphenylmethyl --.

Column 20,
Line 61, please delete "teterahaloborate" and insert therefor -- tetrahaloborate --.

UNITED STATES PATENT AND TRADEMARK OFFICE
CERTIFICATE OF CORRECTION

PATENT NO. : 6,124,484
DATED : September 26, 2000
INVENTOR(S) : Sanghvi et al.

It is certified that error appears in the above-identified patent and that said Letters Patent is hereby corrected as shown below:

<u>Column 21,</u>
Lines 1 and 22, please delete "p-tolyldipheylmethyl" and insert therefor -- p-tolyldiphenylmethyl --.

Signed and Sealed this

Twenty-third Day of April, 2002

Attest:

Attesting Officer

JAMES E. ROGAN
*Director of the United States Patent and Trademark Office*